United States Patent [19]

Purdy

[11] 4,083,884

[45] Apr. 11, 1978

[54] CALCIUM OXIDE MODIFIED ZINC FERRITE OXIDATIVE DEHYDROGENATION CATALYSTS AND USE

[75] Inventor: Charles C. Purdy, Houston, Tex.

[73] Assignee: Petro-Tex Chemical Corporation, Houston, Tex.

[21] Appl. No.: 706,664

[22] Filed: Jul. 19, 1976

[51] Int. Cl.$^2$ .................. B01J 23/58; C07C 11/12
[52] U.S. Cl. ......................... 260/669 A; 260/680 E; 252/473
[58] Field of Search ........... 260/680 R, 680 E, 669 A; 252/473

[56] References Cited

U.S. PATENT DOCUMENTS

| 3,716,589 | 2/1973 | Kotanigawa et al. ............... 252/473 |
| 3,998,760 | 12/1976 | Christman et al. ............... 260/680 E |
| 3,998,902 | 12/1976 | Foster et al. ..................... 260/680 E |

*Primary Examiner*—O. R. Vertiz
*Assistant Examiner*—Brian E. Hearn
*Attorney, Agent, or Firm*—Kenneth H. Johnson

[57] ABSTRACT

Improved oxidative dehydrogenation catalysts are prepared by modifying zinc ferrite oxidative dehydrogenation catalysts with calcium oxide. The resulting catalysts exhibit reduced carbonyl compound production when used in oxidative dehydrogenation.

13 Claims, No Drawings

CALCIUM OXIDE MODIFIED ZINC FERRITE OXIDATIVE DEHYDROGENATION CATALYSTS AND USE

BACKGROUND OF THE INVENTION

The present invention relates to improved oxidative dehydrogenation catalysts and the process of oxidative dehydrogenation employing the improved catalysts. More specifically, the invention relates to modified zinc ferrite catalysts which are effective in substantially reducing the by-product carbonyl compounds, e.g., aldehydes, produced during the oxidative dehydrogenation of hydrocarbons.

Zinc ferrite catalysts have been employed in oxidative dehydrogenation processes to convert saturated and/or unsaturated hydrocarbons to more highly unsaturated hydrocarbons through removal of hydrogen from such hydrocarbons as are known in the art, for example, as shown in U.S. Pat. Nos. 3, 303,235; 3,303,238; 3,607,966; and 3,856,880. These catalysts have proven adaptable to commercial use and appear to be among the best of the various disclosed catalysts for oxidative dehydrogenation. However, zinc ferrite catalysts produce carbonyl compounds as impurities.

Improved processes using zinc ferrite catalysts for the preparation of unsaturated hydrocarbons such as butene, butadiene-1,3, isoprene and styrene are processes, whereby hydrocarbons such as butane, butene, isopentene or ethyl benzene are dehydrogenated at elevated temperatures in the presence of catalysts and oxygen. Superior results and yields of product are thereby obtained. However, the product streams contain not only the desired unsaturated hydrocarbon, but also various oxygenated compounds such as aldehydes and other carbonyl compounds. When air is used as the source of the oxygen, the effluent from the dehydrogenation reactor will contain large quantities of relatively noncondensable gases, such as nitrogen. The gaseous effluent may also contain varying amounts of steam. It is one of the principle objects of this invention to provide a process for the reduction of the carbonyl and other oxygenated compounds in the gaseous product stream containing hydrocarbons.

The oxygenated compounds are a serious contaminant in the unsaturated hydrocarbon product and must be essentially completely removed in order to have a product of suitable purity, e.g., a product having on the order of a few parts per million carbonyl compounds. The essentially complete removal of the oxygenated compound is quite difficult for several reasons. In the first place, the oxygenated compounds constitute only a very minor percentage of the gaseous stream to be purified. Normally, the carbonyl compounds will constitute less than 5 mol percent of the gaseous stream to be purified and more usually may constitute such as less than or up to 2.5 mol percent of the gaseous stream. Generally, the feed stream will contain at least about 10 ppm carbonyl compounds based on the other organic compounds, such as the hydrocarbons. The oxygenated compounds are therefore quite difficult to remove because of their low concentrations in the gaseous stream. In addition, the oxygenated compounds may be difficult to separate from compounds such as hydrocarbons, regardless of their relative concentration. Azeotropes may form between the oxygenated compounds and various hydrocarbons. For instance, an azeotrope is formed between acetaldehyde and butadiene-1,3. It is, therefore, an advantage of this invention to provide modified zinc ferrite catalysts and process having a reduction of carbonyl compounds produced in the oxidative dehydrogenation.

Prior processes have dealt with the separation of oxygenated compounds from oxidative dehydrogenation processes. In U.S. Pat. No. b 3,308,201 and U.S. Pat. No. 3,336,414, oxygenated compounds are removed by scrubbing with an aqueous composition. These processes have the drawback that the carbonyl compounds are transferred to a scrubbing water and must still be disposed of such as by biodegradation. According to U.S. Pat. No. 3,557,238, the carbonyl compounds are condensed with the steam from the reactor effluent, revaporized and fed back to the dehydrogenation reactor. Therefore, one advantage of this invention is to provide an oxidative dehydrogenation process suppressing carbonyl compounds. It is a further advantage to reduce the carbonyl compounds produced without significantly losing reactor product or significantly isomerizing any of the products. A particular feature is to provide a process which is particularly effective in reducing formaldehyde because formaldehyde is difficult to economically separate from aqueous compositions.

SUMMARY OF THE INVENTION

Briefly stated, the present invention lies in the discovery of an improved oxidative dehydrogenation zinc ferrite catalyst modified with a carbonyl suppressing amount of calcium oxide. The term "carbonyl suppressing amount" is used to designate that amount of calcium oxide which, when added to the preformed zinc ferrite, will cause a reduction in the amount of carbonyl produced in an oxidative dehydrogenation of organic compounds, as compared to the same reaction over the zinc ferrite catalyst without the calcium oxide additive. The invention also encompasses the improved oxidative dehydrogenation carried out using the modified zinc ferrite catalyst, having a reduced production of carbonyl compounds.

Preferably, the zinc ferrite catalyst will be modified with from about 1 to 3 weight percent of the calcium oxide based on zinc ferrite in the catalyst.

All references to overall quantities of carbonyl compounds are determined by ASTM Method D-1089 and reported as acetaldehyde. The procedure is modified to exclude the analysis of acetals. Generally, the carbonyl compounds will have from 1 to 8 carbon atoms, e.g., from 1 to 6 carbon atoms when a $C_4$ to $C_6$ compound is being dehydrogenated, and will have from 1 to 2 carbonyl groups. Formaldehyde is included in this definition.

DESCRIPTION OF THE PREFERRED EMBODIMENTS

Oxidative Dehydrogenation Reactants

The catalyst process of this invention can be applied to the dehydrogenation of a wide variety of organic compounds. Such compounds normally will contain from 2 to 20 carbon atoms, at least one

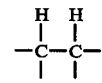

grouping, a boiling point below about 350° C, and may contain other elements, in addition to carbon and hydrogen, such as oxygen, halogens, nitrogen and sulfur. Preferred are compounds having 2 to 12 carbon atoms, and especially preferred, are compounds of 3 to 6 or 8 carbon atoms. Hydrocarbons of the above described carbon content form a preferred group.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustration of dehydrogenation includes propionitrile to acrylonitrile; propionaldehyde to acrolein; ethyl chloride to vinyl chloride; methyl isobutyrate to methyl methacrylate; 2 or 3 chlorobutane-1 or 2,3-dichlorobutane to chloroprene; ethyl pyridine to vinyl pyridine; ethylbenzene to styrene; isopropylbenzene to α-methyl styrene; ethylchlorohexane to styrene; ethyl benzene to styrene; cyclohexane to benzene; ethane to ethylene to acetylene; propane to propylene or methyl acetylene, allene or benzene; isobutane to isobutylene; n-butane to butene and butadiene-1,3; n-butene to butadiene-1,3 and vinyl acetylene; methylbutene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentane to xylenes; and the like.

More specifically, suitable dehydrogenation reactions are the following: acyclic compounds having 4 to 5 nonquaternary contiguous carbon atoms to the corresponding olefins, diolefins, or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbons atoms, and no quaternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 or 3 carbon atoms to the corresponding aromatic with unsaturated side chain, such as ethyl benzene to styrene.

The preferred compounds to be dehydrogenated are hydrocarbons with a particularly preferred class being acyclic nonquaternary hydrocarbons having 4 to 5 contiguous carbon atoms or ethyl benzene and the preferred products are n-butene-1 or 2, butadiene-1,3, vinyl acetylene, 2-methyl-1-butene, 3-methyl-1-butene, 3-methyl-2-butene, isoprene, styrene or mixtures thereof. Especially preferred as feed are n-butene-1 or 2 and methyl butenes and mixtures thereof, such as hydrocarbon mixtures containing these compounds in at least 50 mol percent.

Reaction Condition

The dehydrogenation reaction may be carried out at atmospheric pressure, superatmospheric pressure or at subatmospheric pressure. The total pressure of the system will normally be about or in excess of atmospheric pressure, although subatmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

The temperature for the dehydrogenation reaction generally will be at least about 250° C, such as greater than about 300° or 375° C, and the maximum temperature in the reactor may be about 700° or 800° C, or perhaps higher such as 900° C under certain circumstances. However, excellent results are obtained within the range of or about 350° to 700° C, such as from or about 400° to or about 675° C. The temperatures are measured at the maximum temperature in the dehydrogenation zone.

The organic compound to be dehydrogenated is contacted with oxygen in order for the oxygen to oxidatively dehydrogenate the compound. Oxygen may be fed to the reactor as pure oxygen, as air, as oxygen-enriched air, oxygen mixed with diluents, and so forth. Oxygen may also be added in increments to the dehydrogenation zone. Although determinations regarding the mechanism of reaction are difficult, the process of an oxidative dehydrogenation process is one wherein the predominant mechanism is by the reaction of oxygen with the hydrogen released from the hydrocarbon.

The amount of oxygen employed may vary depending upon the desired result such as conversion, selectivity and the number of hydrogen atoms being removed. Thus, to dehydrogenate butane to butene requires less oxygen than if the reaction proceeds to produce butadiene. Normally, oxygen will be supplied (including all sources, e.g., air to the reactor) in the dehydrogenation zone in an amount from about 0.2 to 1.5, preferably 0.3 to 1.2, mols per mol of $H_2$ being liberated from the organic compound. Expressed in terms of the organic compound being dehydrogenated, the oxygen is supplied in an amount of from about 0.2 to 2.0 mols per mol of organic compound to be dehydrogenated with a preferred range of from about 0.25 to 1.5 mols of oxygen per mol of organic compound.

The gaseous reactants may be conducted through the dehydrogenation zone at a fairly wide range of flow rates. The optimum flow rates will be dependent upon such variables as the temperature of reaction, pressure, particle size, and so forth. Desirable flow rates may be established by one skilled in the art. Generally, the flow rates will be within the range of about 0.10 to 10 liquid volumes of the organic compound to be dehydrogenated per volume of dehydrogenation zone containing catalyst per hour (referred to as LHSV). Usually, the LHSV will be between 0.15 and about 5. For calculation, the volume of a fixed bed dehydrogenation zone containing catalyst is that original void volume of reactor space containing catalyst. The gaseous hourly space velocity (GHSV) is the volume of the hydrocarbon to be dehydrogenated, in the form of vapor calculated under standard conditions of 25° C and 760 mm. of mercury, per volume of reactor space containing catalyst per hour. Generally, the GHSV will be between about 25 and 6400, and excellent results are obtained between about 38 and 3800. Suitable contact times are, for example, from about 0.001 or higher to about 5 or 10 seconds, with particularly good results being obtained between 0.01 and 3 seconds. The contact time is the calculated dwell time of the reaction mixture in the reaction zone, assuming the mols of product mixture are equivalent to the mols of feed mixture. For the purpose of calculation of residence times, the reaction zone is the portion of the reactor containing catalyst.

Preferably, the reaction mixture contains a quantity of steam or a diluent such as nitrogen. These gases serve to reduce the partial pressure of the organic compound; however, the functions of steam in the reaction are severalfold, in that the steam does not act merely as a diluent such as nitrogen. These gases serve to reduce the partial pressure of the organic compound; however, the functions of steam in the reaction are severalfold in that the steam does not act merely as a diluent. Whenever steam is employed in the process of the instant invention, it is employed in an amount generally of from about 2 to about 40 mols of steam per mol of organic compound to be dehydrogenated, with an amount of from about 3 to about 35 mols of steam per mol of organic compound to be hydrogenated being preferred. Especially preferred are amounts of from about 5 to about 30 mols of steam per mol of organic compound to be dehydrogenated, e.g., amount 12 – 20 mols of steam. Whenever a diluent is employed instead of steam, such diluents generally may be used in the same quantities as specified for steam.

In one modification of this invention, halogen is present in the reaction gases. The presence of halogen in the dehydrogenation zone is particularly effective whenever the compound to be dehydrogenated is a saturated hydrocarbon. Whenever halogen is employed in the dehydrogenation zone, it is provided as elemental halogen or a compound of halogen which liberates halogen under the conditions of the dehydrogenation reaction. Suitable sources of halogen include hydrogen iodide, hydrogen bromide and hydrogen chloride; aliphatic halides such as ethyl iodide, methyl bromide, methyl chloride, and 1,2-dibromoethane; cycoaliphatic halides; ammonium iodide, ammonium bromide, ammonium chloride, sulfuryl chloride; metal halides including molten halides; and the like. The halogen also may be liberated partially or entirely by a solid source as disclosed in the process of U.S. Pat. No. 3,130,241 issued Apr. 21, 1964. Mixtures of various sources of halogen may be used. Whenever employed in the process of the instant invention, the amount of halogen employed (calculated as elemental halogen) is from about 0.0001 to about 1.0 mols of halogen per mol of the organic compound to be dehydrogenated with an amount of from about 0.01 to about 0.5 mols of halogen per mol of organic compound being preferred.

Catalysts

The catalyst compositions useful in the present invention include zinc ferrites containing, as the active components thereof, zinc, iron and oxygen in combination as hereinafter described and additionally containing free calcium oxide as a modifier.

The zinc ferrite constituents of the instant catalyst compositions comprise zinc ferrite of the empirical formula $Zn_xFe_yO_z$, wherein $x$ will be from about 0.1 to 2, inclusive, and $y$ can be in the range of about 0.3 to 12, inclusive, and z will vary depending upon the number of oxygen vacancies, but will usually be within the range of about 3 to 18, inclusive. Especially preferred are zinc ferrite compositions wherein the ratio of $y$ to $x$ is from about 2:1 to about 5:1. Although the modified zinc ferrite catalyst may be broadly defined as containing crystalline structures of iron, oxygen and zinc, certain types of catalysts are preferred. Zinc ferrite formation may be accomplished by reacting an active compound of iron with an active compound of zinc. By the term "active compound" is meant a compound which is reactive under the conditions hereinafter described to form the ferrite. The active compounds are suitably oxides or compounds which are converted to oxides during the formation of the ferrite, such as organic and inorganic salts or hydroxides. Active compounds of iron and zinc include the nitrates, hydroxides, hydrates, oxalates, carbonates, acetates, formates, halides, oxides, etc. For example, zinc carbonate may be reacted with iron oxide hydrates to form zinc ferrite. Salts of the desired metals may be coprecipitated and the precipitate heated to form the ferrite. Desired ferrites may be obtained by conducting the reaction to form the ferrite at relatively low temperatures, that is, at temperatures lower than some of the very high temperatures used for the formation of some of the semi-conductor applications. Good results have been obtained by heating the ingredients to a temperature high enough to produce the zinc ferrite, but at conditions no more severe than equivalent to heating to 850° C for 90 minutes in air. Generally, the maximum temperature will be less than 700° C and preferably about 650° C. Methods of preparing zinc ferrite catalyst compositions suitable for use in the process of this invention are disclosed in U.S. Pat. Nos. 3,270,080; 3,284,536; 3,303,234-6; 3,303,238; 3,308,182; 3,334,152; 3,420,912; 3,440,299; 3,342,890 and 3,450,787.

As is apparent from the empirical formula presented herein for zinc ferrite, the ratio of iron to zinc in such ferrite mixtures is not restricted to the stoichiometric ratios as would be present in the simple compound zinc ferrite. In the catalyst compositions of the instant invention, there is present zinc ferrite compound as well as one or more oxides of the constituent cations. For example, if the active compounds are employed such that in the empirical formula $y$ is about 3 and $x$ is 1, the catalyst composition formed therefrom will contain iron oxide in addition to the zinc ferrite formed. Similarly, the zinc ferrite precursor composition may comprise an excess of zinc over the stoichiometric amount to form the ferrite, in which case the resulting catalyst will contain zinc oxide in addition to the zinc ferrite formed.

The preferred zinc ferrite catalyst compositions of the instant invention are those having a face-centered cubic structure. However, the zinc ferrites of the instant invention will not be present in the most highly oriented crystalline structure because it has been found that superior results may be obtained with catalysts wherein the zinc ferrite is relatively disordered. Such catalyst compositions may be obtained by conducting the reaction to form the zinc ferrite at relatively low temperatures as described herein.

The zinc ferrite catalyst compositions of the present invention can be identified by their characteristic X-ray diffraction patterns. The preferred catalyst compositions will generally have X-ray diffraction peaks at d-spacings within or about 4.83 to 4.89; 2.95 to 3.01; 2.51 to 2.57; 2.40 to 2.46; 2.08 to 2.14; 1.69 to 1.75; 1.59 to 1.65 and 1.46 to 1.52, with the most intense peak being between 2.51 to 2.57. Particularly preferred catalysts will have d-spacings within or about 4.81 to 4.88; 2.96 to 3.00; 2.52 to 2.56; 2.41 to 2.45; 2.09 to 2.13; 1.70 to 1.74; 1.60 to 1.64; and 1.47 to 1.51, with the most intense peak falling within or about 2.52 to 2.56. These X-ray determinations are suitably run with a cobalt tube.

The zinc ferrite is preformed and the calcium oxide or calcium oxide precursor is added to the preformed zinc ferrite. The calcium is not incorporated into the ferrite, but exist in the free state in intimate association with the zinc ferrite and any other components or modifiers of the catalyst.

The calcium oxide catalyst modifier of the instant invention can be employed in the form of calcium oxide itself or a calcium compound which will be converted to calcium oxide under the oxidative dehydrogenation reaction conditions set forth herein, i.e., a calcium oxide precursor are more particularly calcium compounds such as the oxides and salts, including the carbonate, nitrate, chloride, acetate, and the like. Preferred calcium oxide precursors are calcium nitrate, calcium carbonate, calcium chloride and calcium acetate. Particularly preferred are calcium nitrate and calcium acetate.

It has been found that not all calcium oxide precursors are equally as effective when incorporated into the catalyst for reducing the carbonyl compounds. The final or principle form of the calcium compound after either pretreatment or startup of the oxidative dehydrogenation is the oxide, but small residual quantities of a precursor might act as an activator or promoter.

It has been found that calcium nitrate or calcium acetate produce particularly effective modified zinc ferrite catalyst compositions.

The calcium oxide or calcium oxide precursor catalyst modifier may be added to the zinc ferrite by any suitable method. The modifier is incorporated into the catalyst after the zinc ferrite has been formed. If a catalyst support or carrier is employed, one convenient method is to form a slurry of the modifier with the zinc ferrite prior to coating on the support. Although aqueous mediums will generally be employed when coating a support with the catalyst constituents, it is contemplated that nonaqueous systems can also be employed, if desired, in the preparation of the catalyst. Another suitable method for incorporating the modifier into the zinc ferrite composition is by dry-mixing the components.

The calcium oxide modifier is present in the zinc ferrite catalyst composition in a carbonyl suppressing amount. Generally, a carbonyl suppressing amount of calcium oxide will be not more than about 5% by weight, based on the total weight of the zinc ferrite composition present. Amounts of calcium oxide of from about 0.5 to 5% are satisfactory, with amounts of from about 1 to about 3%, based on the weight of zinc ferrite composition being preferred.

In addition to the calcium oxide, the zinc ferrite catalysts may contain various components which also serve as promoters, initiators, stabilizers or the like. Other additives are sulfur, phosphorus, silicon, boron, magnesium, manganese or mixtures thereof, for example, sulfates, sulfites, sulfides, alkylmercaptans, sulfuric acid, phosphates, phosphoric acid, silica, silicates, boron trifluoride, magnesium oxide, manganese oxide and the like. Such additives are disclosed in U.S. Pat. Nos. 3,247,278; 3,270,080; 3,303,238; 3,324,195; 3,398,100; 3,937,746.

Catalyst binding agents and fillers may also be used, but these will not ordinarily exceed about 50 percent or 75 percent by weight of the catalytic surface, and the described catalytic compositions will preferably constitute the main active constituent. These other binding agents and fillers will preferably be essentially inert. Preferred catalysts are those that have as a catalytic surface exposed to the reaction gases at least 25 or preferably 50 percent of the defined catalytic surface exposed to the reaction gases at least 25 or preferably 50 percent of the defined catalytic surface. The catalytic surface may be introduced as such or it may be deposited on a carrier by methods known in the art such as by preparing an aqueous solution or dispersion of a catalytic material and mixing the carrier with the solution or dispersion until the active ingredients are coated on the carrier. If a carrier is utilized, very useful carriers are silicon carbide, aluminum oxide, pumice, and the like. Other known catalyst carriers may be employed. When carriers are used, the amount of catalyst on the carrier will suitably be between about 5 to 75 weight percent of the total weight of the active catalytic material plus carrier. Another method for introducing the required surface is to utilize as a reactor a small diameter tube wherein the tube wall is catalytic or is coated with catalytic material. Other methods may be utilized to introduce the catalytic surface such as by the use of rods, wires, mesh, or shreds, and the like, of catalytic material. The catalytic surface described is the surface which is exposed in the dehydrogenation zone to the reaction gases, that is, e.g., if a catalyst carrier is used, the composition described as a catalyst refers to the composition of the surface and not to the total composition of the surface coating plus carrier.

The catalyst compositions of the instant invention may be activated prior to use by treatment with a reducing gas, such as, for example, hydrogen or hydrocarbons. For example, the reduction may be effected with hydrogen at a temperature of from about 500° to about 1,000° F, with temperatures of from about 950° to about 1,000° F being preferred. The time required for reduction will be dependent upon the temperature selected for the reducing step and will generally be from about ten minutes to about 2 to 3 hours.

The process of this invention is suitably deployed with a fixed catalyst bed in the dehydrogenation zone.

The following examples are illustrative only of the invention and are not intended to limit the invention. All percentages are weight percent unless specified otherwise. All conversions, selectivities and yields are expressed in mol percent of the designated feed. The presence of zinc ferrite was determined by infrared analysis. Product analysis was by gas chromatography.

EXAMPLES 1-8

In these examples an oxidative dehydrogenation of a normal butene (~98 mol%): LHSV 1.5; mol ratio oxygen to steam to butenes; 0.55/(10 to 20)/1.

The reactor used consists of two 23-½ inch electric combustion furnaces mounted vertically one over the other about three inches apart. Each unit is capable of independent temperature control. Each of the two furnaces house a 24 × 1 inch I.D., 316 stainless steel tube. These two tubes are joined by a common connection located between the two furnaces. The top tube contains an inert packing, e.g., 6 × 6 mm Vycor raschig rings and is used to vaporize, mix and preheat reactants and/or diluents before they pass downflow over the catalyst bed contained in the bottom tube of the reactor system. The bottom tube contains 125 cc of catalyst Vycor raschig rings (6 × 6 mm) are used to support the catalyst at a desired level in the tube and also to fill any void space remaining in the tube above the level of the top of the catalyst bed. The temperature of the catalyst bed is measured with thermocouples inserted into a ¼ inch, 316 ss thermowell located inside and coaxial with the reaction tube. All of the reaction examples described herein were carried out in reactors of the same design.

The zinc ferrite had a ratio of $Fe_2O_3/ZnO$ of 2.29 and was prepared by the general procedure:

been detrimental to oxidative dehydrogenation as shown by the C/S/Y.

TABLE I

| Example | Wt. % CaO (added as) | Activation | | | | Reaction Conditions | | Results |
|---|---|---|---|---|---|---|---|---|
| | | Time Hrs | Temp °F | ml/ min $H_2$ | Steam cc $H_2O$ min | Hrs On Stream | Ti/Tmax °F | Mole % C/S/Y |
| 1 | 2.0 wt. % CaO as $(Ca(NO_3)_2)$ | 2 | 1000 | 0 | 6 | 989 | 654/984 | 78.3/95.5/74.8 |
| 2 | 5.0 wt. % CaO as $(Ca(NO_3)_2)$ | 2 | 1000 | 0 | 12 | 169 | 642/986 | 62.2/93/3/58 |
| 3 | 1 wt. % CaO as $(Ca(NO_3)_2)$ | 2 | 1000 | 400 | 6 | 363 | 638/965 | 79.2/96.7/76.6 |
| 4 | 1 wt. % CaO as $(Ca(NO_3)_2)$ | 2 | 1000 | 0 | 12 | 473 | 642/964 | 79.8/96.7/77.2 |
| 5 | 2 wt. % CaO as $(Ca(NO_3)_2)$ | 2 | 1000 | 400 | 6 | 844 | 646/980 | 77.6/96.3/74.9 |
| 6 | 2.0 wt. % CaO as $(CaCO_3)$ | 2 | 1000 | 400 | 6 | 761 | 639/978 | 73.7/95/4/70.3 |
| 7 | 2.0 wt. % CaO as $(Ca(C_2H_3O_2)_2 \cdot H_2O)$ | 2 | 1000 | 400 | 6 | 714 | 620/902 | 79.4/96.1/76.3 |
| 8* | 2.0 wt. % CaO as $(CaCl_2)$ | | | | | 42 | 610/970 | 70.2/95.6/67.1 |

*Mole ratio $O_2$/Stream/Butene = 0.52/15/1

```
76.14 # Fe2O3·H2O     (87% Fe2O3)
41.72 # ZnCO3         (66.9% ZnO)
 6.92 # MnCO3         (61.7% MnO)
 2.55 # ZnCl2         (61.92% ZnO)
```

The above are added to demineralized water to give 28% solid slurry and blended then dried. The dried powder is granulated and calcined in a rotary kiln at 5#/hr, nitrogen atmosphere, at 1060°–1070° F. The calcined actives with the appropriate amount of calcium compound to provide the calcium oxide shown in Table I are then placed in a ribbon blender and a solution of phosphoric acid in water is added at the rate of 180 cc solution/# of Zn ferrite actives. Enough $H_3PO_4$ is added to give 3% $H_3PO_4$ based on the weight of Zn ferrite. The blended material is pelleted (1/16 inches) and dried. The compositions were placed in the reactor, activated, then employed in the oxidative dehydrogenation of butenes. The activation and results are shown in Table I. The following abbreviations are used in the Tables:

- ml - milliliters
- cc - cubic centimeters
- min - minutes
- Ti - inlet temperature
- Tmax - maximum temperature
- C - conversion
- S - selectivity
- Y - yield Each of the calcium oxide modified catalysts, according to the present invention, exhibited substantial reduction in the amount of formaldehyde produced, e.g., from 50 to 95% less than normally observed to be produced with substantially the same zinc ferrite catalyst without CaO. (The unmodified catalysts have been extensively observed in pilot plant and commercial operations.) The presence of the CaO, however, has not

EXAMPLES 9 and 10

In these examples a zinc ferrite prepared as described above with 2% CaO added as the nitrate was quantitatively observed in regard to the carbonyl compounds produced (Example 9) and compared with a similar unmodified zinc ferrite. These observations confirmed the prior data. The results are shown in Table II.

TABLE II

Catalyst activation 1000° F for 2 hours in steam (12 cc/min $H_2O$) and 400 ml/min $H_2$, mole ratio $O_2$/Steam/Butene = .55/15/1, LHSV = 2

| Catalyst | Temp. Ti/Tmax °F | Results | | | |
|---|---|---|---|---|---|
| | | C/S/Y Mole% | Carbonyls ppm | | |
| | | | Acetaldehyde | Furan | Acrolein |
| 9. Zn ferrite + 2% CaO | 630/1020 | 75.1/95.9/72 | 160 | 130 | 710 |
| 10. Zn ferrite | 645/1025 | 78.7/95.8/75.4 | 2904 | 2105 | 1019 |

The invention claimed is:

1. A novel catalyst composition suitable for oxidative dehydrogenation of organic compounds in the presence of molecular oxygen consisting essentially of a zinc ferrite composition having the empirical formula $$Zn_xFe_yO_z$$

wherein x is from about 0.1 to about 2, y is from 0.3 to about 12, and z is from about 3 to about 18 and additionally containing free calcium oxide as a suppressor of carbonyl compounds in a carbonyl suppressing amount.

2. The novel catalyst according to claim 1 wherein the calcium oxide is present in an amount of from about 0.5 to 5 weight percent based on the weight of zinc ferrite.

3. The novel catalyst according to claim 2 wherein the calcium oxide is present in an amount of from 1 to 3 weight percent based on the weight of zinc ferrite.

4. The novel catalyst according to claim 1 wherein the ratio of y to x is about 2:1 to about 5:1.

5. A novel catalyst composition suitable for oxidative dehydrogenation of organic compounds in the presence of molecular oxygen consisting essentially of zinc ferrite composition having the empirical formula $$Zn_xFe_yO_z$$

wherein x is from about 0.1 to about 2, y is from 0.3 to about 12, and z is from about 3 to 18 and additionally containing free calcium oxide as a carbonyl suppressor in an amount of from about 0.5 to about 5 weight percent based on the weight of zinc ferrite composition prepared by intimately mixing preformed zinc ferrite and calcium oxide or a compound which will convert to calcium oxide under the condition of oxidative dehydrogenation.

6. In the process of oxidative dehydrogenation of organic compounds having from about 2 to about 20 carbon atoms and at least one

group in the presence of molecular oxygen and a zinc ferrite catalyst composition having the empirical formula $Zn_xFe_yO_z$ wherein $x$ is from 0.1 to about 2, $y$ is about 0.3 to about 12 and $z$ is about 3 to 18 at a temperature of from 250° C to about 900° C to thereby produce a dehydrogenated compound having the same number of carbon atoms, wherein the improvement comprises incorporating into said catalyst composition calcium oxide as a carbonyl suppressor in an amount of from about 0.5 to about 5 weight percent based on the weight of the zinc ferrite composition.

7. The process of claim 6 wherein the oxidative dehydrogenation is carried out in the presence of from about 0.2 to about 2.0 mols of oxygen per mol of organic compound present.

8. The process of claim 7 wherein the oxidative dehydrogenation is carried out in the additional presence of from about 2 to about 40 mols of diluent per mol of organic compound present, said diluent being selected from the group of steam and nitrogen.

9. The process according to claim 6 wherein the organic compound is an acyclic hydrocarbon having 4 to 5 nonquaternary contiguous carbon atoms or ethylbenzene.

10. The process according to claim 9 wherein said hydrocarbon consists essentially of normal butenes.

11. The catalyst according to claim 5 wherein said compound which will convert to calcium oxide is calcium nitrate, calcium carbonate, calcium chloride or calcium acetate.

12. The catalyst according to claim 11 wherein said compound is calcium nitrate.

13. The catalyst according to claim 11 wherein said compound is calcium acetate.

* * * * *